US008382889B1

(12) United States Patent
Brizius

(10) Patent No.: US 8,382,889 B1
(45) Date of Patent: Feb. 26, 2013

(54) DENDRITIC STARCH-BASED DEXTRIN ADHESIVES

(75) Inventor: Glen Leon Brizius, Augusta, GA (US)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 13/389,582

(22) PCT Filed: Nov. 9, 2011

(86) PCT No.: PCT/US2011/059942
§ 371 (c)(1),
(2), (4) Date: Feb. 8, 2012

(51) Int. Cl.
*C09J 11/06* (2006.01)
*C09J 11/08* (2006.01)
*C09J 103/02* (2006.01)

(52) U.S. Cl. ............. 106/205.1; 106/205.72; 106/209.1; 106/215.5

(58) Field of Classification Search ............... 106/205.1, 106/205.72, 209.1, 215.5
See application file for complete search history.

(56) References Cited

U.S. PATENT DOCUMENTS

| 2,051,025 | A | 8/1936 | Bauer |
| 2,102,937 | A | 12/1937 | Bauer |
| 2,212,557 | A | 8/1940 | Bauer |
| 3,607,395 | A | 9/1971 | Stephenson |
| 6,613,152 | B1 | 9/2003 | Maas et al. |
| 2008/0312344 | A1 | 12/2008 | Liskamp et al. |
| 2009/0196847 | A1 | 8/2009 | Cloninger et al. |
| 2009/0306310 | A1 | 12/2009 | Wu et al. |
| 2010/0036054 | A1 | 2/2010 | Hutchings et al. |

OTHER PUBLICATIONS

International Search Report and Written Opinion for PCT/US2011/059942 dated Jan. 5, 2012.
LaserFocusWorld, Multimodal Nonlinear Optical Imaging, http://www.laserfocusworld.com/whitepapers/2012/01/semrockinc.html (Printed from Internet Jan. 19, 2012).
Volatile Organic Compounds, Health Effects Fact Sheet, Colorado Department of Public Health and Environment (Nov. 2000).
An Introduction to Indoor Air Quality (IAQ), Volatile Organic Compounds (VOCs), http://www.eap.gov/iaq/voc.html (Printed from Internet Jan. 19, 2012).
Peacock Allied Products Pvt. Ltd., Modified Starches, Dextrin and Starch Based Adhesives/Gums, http://www.dextrinadhesives.com (Printed from Internet Jan. 19, 2012).
Nepogodiev et al., Synthesis of triazole-linked pseudo-starch fragments, *Carbohydr Res* (Feb. 26, 2007), 342(3-4):529-540 (Abstract).
Isomeric Compounds of Trihydroxybenzene Molecule Structure, 2,3,4-Trihdroxybenzoic Acid, http://www.chemicalland21.com/lifescience/UH/2,3,4-Trihydroxybenzoic%20ACID (Printed from Internet Jan. 17, 2012).
Ding et al., A highly efficient and selective synthesis of 1,2,3-triazole linked saccharide nucleosides via "click chemistry"., *Nucleosides Nucleotides Nucleic Acids* (Apr. 2008), 27(4):368-375 (Abstract).
Baumann et al., Carbohydrate Polymers as Adhesives, Handbook of Adhesive Technology, Chapter 15, pp. 299-313, New York: Marcel Dekker, Inc. (1994).
Hein et al., Click Chemistry, a Powerful Tool for Pharmaceutical Sciences, *Pharm Res* (Oct. 2008), 25(10):2216-2230.
de Oliveira et al., Efficient Synthesis of Some Unsaturated (1,2,3)-Triazole-Linked Glycoconjugates, *Journal of Carbohydrate Chemistry* (Apr. 3, 2006), 25:407-425.
Koumbis et al., 1,3-Dipolar Cycloadditions in the Synthesis of Carbohydrate Mimics. Part 3: Azides, Diazo Compounds and Other Dipoles, *Current Organic Chemistry* (2003), 7(8):771-797.
Hawker et al., Preparation of Polymers with Controlled Molecular Architecture. A New Convergent Approach to Dendritic Macromolecules, *J. Am. Chem. Soc.* (Jan. 16, 1990), 112(21):7638-7647.
Díaz et al., Click Chemistry in Material Synthesis. 1. Adhesive Polymers from Copper-Catalyzed Azide-Alkyne Cycloaddition, Department of Chemistry, The Scripps Research Institute, La Jolla, CA (Apr. 16, 2004), 42:4392-4403.
Lazarus, Adhesives Based on Starch, Adhesion vol. 7, Chapter 10, pp. 197-219, Elsevier Science Publishing Co., Inc., New York, (1983).
Jarowenko, Starch Based Adhesives, Handbook of Adhesives, Chapter 12 (1977), National Starch and Chemical Corporation, Bridgewater, New Jersey, pp. 192-211.

*Primary Examiner* — David M Brunsman
(74) *Attorney, Agent, or Firm* — Pepper Hamilton LLP

(57) ABSTRACT

A modified starch-based adhesive including a starch-based adhesive and an additive, the additive including a dendron, a sugar unit bound to the dendron, and an antimicrobial agent bound to the dendron and, a method of synthesizing the additive including providing a dendron, binding a linker molecule to the dendron, binding a sugar unit to the linker molecule, and binding an antimicrobial agent to the linker molecule.

32 Claims, No Drawings

DENDRITIC STARCH-BASED DEXTRIN ADHESIVES

CLAIM OF PRIORITY

This application is a U.S. national stage filing under 35 U.S.C. §371 of International Application No. PCT/US2011/059942 filed Nov. 9, 2011 entitled "Dendritic Starch-Based Dextrin Adhesives," the disclosure of which is incorporated by reference in its entirety.

BACKGROUND

Modern society is extremely dependent on a steady supply of adhesives. Adhesives are used in many non-food consumer products, including books, fabricated building materials, apparel and house wares. With such widespread distribution and usage, the health effects of consumers' exposure to these adhesive formulations should be considered. Many currently available adhesive products use petroleum-based starting materials and require organic solvents. As these adhesives cure, the organic solvents are released in the form of potentially harmful or irritating volatile organic compounds (VOCs). VOCs can be harmful to human and animal health, and are a significant cause of indoor air outdoor water supply pollution.

Water-based (water soluble) adhesives represent an attractive alternative to petroleum-based adhesives, as water is inherently nontoxic, non-flammable, and safe to handle. Moreover, preparation of such an adhesive can be derived almost entirely from natural/renewable sources which do not produce VOCs upon curing. One such class of water-based adhesives are the dextrin-based adhesives. Dextrins are low molecular weight carbohydrates that are readily produced via hydrolysis of plant starch. This is achieved by dry roasting starch in the presence of an acid catalyst. Corn starch is the most commonly used starch due to its abundance and low costs. Potato, tapioca and sago starches are other substrates that can be easily converted to dextrin. More specifically, dextrins are oligomers of D-glucose linked by either $\alpha$-(1,4) or $\alpha$-(1,6) glycosidic bonds. Given that these adhesives are water soluble they can therefore be distributed as water-based solutions. The majority of starch-based adhesives are used in the paper and textile industries as binders and sizing materials as well as glues and pastes.

Dextrins fall into three classes: white dextrins, yellow dextrins and British gums. These classes are differentiated by their respective dry roasting times, temperatures and amounts of catalyst used. British gums are typically dry roasted for 10 to 24 hours at temperatures between 150° C. and 180° C. in the presence of small amounts of acid catalyst. British gums are the highest molecular weight dextrin fragments, and as such they typically form the strongest adhesives. The pendant hydroxyl groups form an extended network of inter- and intramolecular hydrogen bonds producing a strong adhesive force. However, the extensive hydrogen bonding network makes these longer fragments of British gum dextrins less soluble in water because the crystalline hydrogen-bonded domains are difficult to separate and dissolve. Because of this, the utility of these starch-based dextrin adhesives is limited as the maximum solids concentration of the dextrin fragments in the water solvent carrier is only about 25% (w/v). In addition, these types of adhesives are susceptible to colonization by a variety of microbes including molds and fungi which can decrease the effective lifetime of the adhesive and the product into which it is incorporated.

SUMMARY

In an embodiment, a starch-based adhesive additive includes a dendron, a sugar unit bound to the dendron, and an antimicrobial agent bound to the dendron.

In another embodiment, a modified starch-based adhesive includes a starch-based adhesive and an additive, the additive including a dendron, a sugar unit bound to the dendron, and an antimicrobial agent bound to the dendron.

In yet another embodiment, a method of synthesizing an additive includes providing a dendron, binding a linker molecule to the dendron, binding a sugar unit to the linker molecule, and binding an antimicrobial agent to the linker molecule.

In an embodiment, a method of forming a modified a starch-based adhesive includes addition of an additive including a dendron, a sugar unit bound to the dendron, and antimicrobial agent bound to the dendron to a starch-based adhesive.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

A chemical formulation with the ability to disrupt the crystalline hydrogen bonding network so as to increase solubility of the adhesive as well as conferring antimicrobial properties to the adhesive would provide a highly desirable additive for a water-based adhesive otherwise lacking these properties. The embodiments described herein provide adhesive additives with antimicrobial properties capable of increasing adhesive solubility for multiple applications.

Various embodiments are directed to starch-based dextrin adhesive additives and methods of their preparation and use. Although starch-based dextrin adhesives are attractive due to their low cost and adhesive strength, their widespread use is hindered by low water solubility and a susceptibility to colonization with mold, which shortens the lifespan of the adhesive. The additives of such embodiments are comprised of one or more functional molecular units covalently linked to one another. Such additives, when added to a starch-based dextrin adhesive in small amounts, may impart a variety of desirable properties such as, for example, antimicrobial properties and increased water solubility in a single additive component. Further embodiments include methods for the synthesis of an additive, as well as additive-adhesive mixtures, methods of using the additives, and methods of using the modified adhesives formed upon addition of the additive to an uncured starch-based adhesive.

Properties such as viscosity, solids content, stability, tack, slip, substrate penetration, drying rate, flexibility, water and microbial resistance, and cost are largely determined by the type of adhesive used; however, certain properties can be modulated by providing additives to adhesive compositions. For example, Borax is a commonly used additive added to starch-based adhesives as a tackifier and viscosity stabilizer, and urea acts as a plasticizer and reduces the viscosity of an adhesive preparation.

Adhesive Additives

The additives of such embodiments include compositions that confer a property on an adhesive by insertion into the adhesive thereby becoming an integral part of the cured adhesive. A "functional molecular unit" of the additives of embodiments can include monomeric or polymeric moieties that confer one or more desirable properties on the adhesive when included as part of the multi-functional additive. Desirable properties are defined as properties that impart positive effects on the adhesive such that the physical properties of the adhesive are enhanced or new properties are added. For example, in some embodiments, the additive can include functional molecular units that act as bulking agents capable of disrupting the crystalline hydrogen bonding network of the adhesive, and in other embodiments, a functional molecular unit may act as an antimicrobial agent. In certain embodiments, the additive may further include at least one sugar unit that may enable integration of the additive into the adhesive, and in other embodiments, the functional molecular units and/or sugar units can be covalently linked by a linker molecule. In some embodiments, an adhesive containing one or more additives of the present invention make the cured adhesive more pliable, more resistant to chipping, more resistant to cracking, or more resistant to microbial growth than a cured sample of the same adhesive in the absence of one or more additives.

In some embodiments, two or more molecular functional units can be covalently linked to one another through a molecular linker, and in other embodiments, two or more molecular functional units can be linked to one another and a sugar unit through a molecular linker. The molecular linker in such embodiments acts as a hub and connecting individual molecular functional units. Thus, various molecular linkers may include two or more reactive moieties extending from a central moiety. For example, in some embodiments, the linker may be 1,3,5-tris(bromomethyl)benzene, which includes a central substituted benzene ring with bromomethyl reactive moieties at the 1, 3, and 5 positions. Similar molecular linkers can include any compound having a central aryl groups, such as, benzene, biphenyl, naphthalene, fluoranthene, phenanthrene, perylene, coronene, cycloalkyl and cycloalkenes, such as, cylcohexane, cyclopentanes cyclopentyldienes, and substituted aryl and cycloalkyl and cycloalkenes such as, for example, pyridines, pyrimidines, imidizoles, piperidines, morpholines, thiophenes, diazoles, pyrroles, furans, and the like. In still other embodiments, the linker may be a linear or branched alkyl or alkene with one or more reactive groups associated with carbons along the alkyl or alkene chain. For example, in some embodiments, the molecular linker may be a triglyceride.

Reactive moieties can be positioned at any location on the central moiety, and in certain embodiments, the reactive moieties may be spaced apart to allow the reactive groups of each reactive moiety to individually react with molecular functional units. Embodiments are not limited to any particular reactive moiety, and in some embodiments, the reactive moiety may at least include one reactive group such as, for example, alkene, alkyne, halide, ester, epoxide, aziridine, carboxylic acid, acid chloride, carbonates, aldehydes, hydroxyl, amine, oxide, thiols, imino, imido, cyano, sulfonic acids, sulfonic esters, sulfhydryl, and the like. In some embodiments, the reactive group may be directly linked to the central moiety, and in other embodiments, the reactive group may be spaced from the central moiety by, for example, an alkyl, alkene, or alkyne. Such spacers may include from 1 to about 10 carbon atoms and may include at least one reactive group. Particular examples, of suitable reactive groups include methylbromide, ethylbromide, acetic acid, propionic acid, propyne butyne, pentyne, methylnitrile, ethylnitrile, propionitrile, and the like.

In some embodiments, the additive may include a functional molecular unit capable of providing steric bulk covalently associated with the molecular linker. Such functional molecular units may confer increased water solubility of the adhesive by disruption the network of hydrogen bonds found within the adhesive molecular structure. Without wishing to be bound by theory, disrupting the crystalline hydrogen-bonding network of, for example, a dextrin adhesive by breaking hydrogen bonds may increase the solubility of the adhesive in water. Molecular functional units that provide steric bulk may also provide areas of amorphous packing among tightly associated starch strands allowing for greater distribution of ultra-high-solid dextrin adhesives in an aqueous carrier. Currently known suspensions of adhesives in water are limited to less than about 25% solids due to the relatively low solubility of unmodified dextrin-based adhesives. Adhesives including a multi-functional additive having at least one multi-functional unit that acts a water-solubilizing plasticizer and provides steric bulk may be flexible and highly water-soluble prior to curing, and such adhesives may include 85% or greater solids. By adding a water-solubilizing plasticizer the additive is expected to disrupt the hydrogen bond crystalline network resulting in increased solubility of the adhesive, and a cured adhesive that is less prone to chipping and more resistant to physical deformation.

In particular embodiments, the molecular functional unit conferring steric bulk can be a dendritic polymer. "Dendritic polymers," or "dendrimers," as used herein encompass hyperbranched polymers, arboresent polymers, fractal polymers, and starburst polymers. In general, dendritic polymers have a central core, an interior structure having a plurality of branches extending away from the central core in every direction, and an exterior surface with numerous end groups. Dendrimeric polymers can be constructed with tight control of size, shape topology, flexibility, and surface groups. For example, in what is known as divergent synthesis, dendritic polymers are created by reacting an initiator core in high-yield iterative reaction sequences to build symmetrical branches radiating from the core with well-defined surface groups. In what is known as convergent synthesis, dendritic wedges are constructed from the periphery inwards towards a focal point and then several dendritic wedges are coupled at the focal points with a polyfunctional core. Dendritic syntheses can form concentric layers, known as generations, with each generation doubling the molecular mass and the number of reactive groups at the branch ends so that the end generation dendrimer is a highly pure, uniform monodisperse macromolecule that solubilizes readily over a range of conditions. These properties allow a dendron to exert significant steric bulk or steric hindrance when it is used in an additive so as to disrupt or prevent the formation of hydrogen bonds within an adhesive.

As dendrimers grow with each generation, the steric constraints from congestion of the branches force the polymer shape to change from a starfish-shaped molecule to a globular molecule. Dendritic growth, shape and topology are controlled by the core, the interior branch structure and the surface groups. Dendrimers expand symmetrically in a way that maintains a constant terminal surface group area. In general, dendritic growth becomes self-limiting as steric congestion of the surface reactive sites precludes further chemical modification.

Dendritic surfaces can have from 3 to 3072 end groups available for surface chemistry and the number of end groups depends on the type of dendrimer structure (which defines steric congestion) and the dendrimer generation. Amino terminated dendrimers react with, e.g., Michael acceptors (e.g. $CH_2\!=\!CHCO_2H$), α-haloesters, epoxides, aziridines, activated carboxylic acids, acid chlorides, benzyl halides, carbonates, or aldehydes. Hydroxyl terminated dendrimers react with, e.g., halosulfonic esters, activated carboxylic acids and acid chlorides. Ester and acid terminated dendrimers react with, e.g., amines, and halide terminated dendrimers react with, e.g., amines and alkoxide and thioalkoxide anions. Other reactive surface groups include carboxyhalide, imino, imido, alkylamino, dialkylamino, alkylarylamino, cyano, sulfonic esters, dithiopyridyl and sulfhydryl, among others. Different surface groups may be present on different dendrons or different distal groups of a dendron. The dendrimer can be solution processable i.e. the surface groups are such that the dendrimer can be dissolved in a solvent. Less reactive or non-reactive end groups also exist. For example, ether or alkyl end groups can be used that are largely non-reactive toward most reagents and conditions. In some embodiments, only the steric demands of the dendron are desired and end group functionality is avoided. In a particular embodiment, a non-reactive end group such as an alkane or ether would be desirable if the synthesis does not allow for a reactive end group to be present such as when the reactive surface of the dendrimer would hinder construction of the overall molecule.

Dendritic polymers useful in embodiments include, but are not limited to, symmetrical and unsymmetrical branching dendrimers or dendrons, cascade molecules, arborols, and the like. In certain embodiments, the dendritic polymers can be dense star polymers. It will be appreciated that one or more of the dendrons attached to the core (provided that at least one dendron is a specified conjugated dendron) can be unconjugated. Typically such dendrons include ether-type aryl dendrons, for example where benzene rings are connected via a methyleneoxy link. It will also be appreciated that when there is more than one dendron, the dendrons can be of the same or different generation (generation level is determined by the number of sets of branching points). It may be advantageous for at least one dendron to be of the second, or higher, generation to provide the required solution processing properties.

In some embodiments, t-butyl and alkoxy groups have been used as surface groups on a dendrimer to achieve solubility in organic solvents and water. In addition, the choice of dendron and/or surface group can allow the formation of blends with dendrimers (organic or organometallic), polymer or molecular compounds. In some embodiments, a dendron can include a single chemically addressable group called the focal point from which repeatedly branched low molecular weight molecules are covalently attached to form a polymeric hyperbranched macromolecule. Dendritic molecules such as these further are characterized by structural perfection and their ability to form spherical three dimensional structures. In particular embodiments, a dendron can be a Frechet-type dendron. Without wishing to be bound by theory, the larger the dendron the greater the steric bulk that will be exerted on the adhesive's crystalline network and hence the greater the water solubility increase conferred by the additive containing a particular dendron.

In certain embodiments, the dendron can be a poly (alkyl aryl ether) dendrimer, a generation 3 Frechet-type poly (aryl ether) dendron, a generation 4 Frechet-type poly (aryl ether) dendron, or a generation 5 Frechet-type poly (aryl ether) dendron. In other embodiments, the dendron can be an aryl ether dendrimer, or a poly (amido amine) dendrimer, also known as a PAMAM or Starburst dendrimer. In yet other embodiments, a dendron will be selected that confers appropriate steric size and bulk with only a single functional end group unblocked to enable connection to the central core molecule.

In some embodiments, the additives can include molecular functional units that provide antimicrobial properties to an adhesive. In these embodiments, the combination of the additive with an adhesive to form a adhesive, results in the adhesive becoming more resistant to growth of at least one of mold, fungus, bacteria, and combinations thereof than the same adhesive in the absence of the additive. Embodiments are not limited to a particular type of antimicrobial agent. For example, the antimicrobial agents may provide anti-bacterial, anti-viral, anti-fungal, anti-mold activities, and the like and combinations thereof. In some embodiments, the antimicrobial agent can be a phenol or polyphenol. Phenol or polyphenol units offer microbial resistance when the additive is present in the cured adhesive, which is a feature lacking in current dextrin adhesive formulations. Examples of phenol and polyphenol units include gallic acid, modified forms of gallic acid including alkyl esters of gallic acid, and combinations thereof. In other embodiments, the antimicrobial agent can be an O-alkyl quaternary ammonium salt such as, but not limited to, benzalkonium chloride, benzethonium chloride, methylbenzethonium chloride, cetalkonium chloride, cetylpyridinium chloride, cetrimonium, cetrimide, dofanium chloride, tetraethylammonium bromide, didecyldimethylammonium chloride, domiphen bromide, and combinations thereof. In these embodiments, the O-alkyl quaternary ammonium salt has one ethyl group substituted for an ethylene group ($-CH_2CH_2-$) allowing for salt to be tethered to a linker molecule within the additive. In a particular embodiment, the antimicrobial agent comprises a quaternary ammonium salt having a structure of the formula O-alkyl-$NR^1R^2R^3X$, wherein $R^1$-$R^3$ are alkyl chains, and wherein X is a counterion such as a chloride ion. In still other embodiments, the antimicrobial agent can be an organic acid. In yet other embodiments, the antimicrobial agent can be 4-hydroxybenzoic acid, a hydroxytyrosol. In some embodiments the additive can include more than one particular antimicrobial agent.

In some embodiments, the addition of a the additives of the present invention results in a modified adhesive that is more resistant to growth of at least one of mold, fungus, bacteria, and combinations thereof than the same adhesive in the absence of the additive.

To conform to the "click" chemistry process, the antimicrobial agent preferably contains an O-alkyl functional group that allows for tethering to the molecular linker. In yet other embodiments the antimicrobial agent contains an ether or ester group that allows tethering to the molecular linker. In other embodiments, alcohol terminated antimicrobial agents are well suited for tethering to a central benzene ring and can also connect to the large variety of reactive groups that may be present around a center benzene. The resulting complexes or linkers and antimicrobial agents are highly stable.

In further embodiments, the additive may include one or more sugar units that may facilitate insertion of the additive into the adhesive macromolecular structure. Embodiments are not limited to any particular type of sugar because essentially any sugar molecule can facilitate insertion into the macromolecular structure of the adhesive. For example, in some embodiments, the sugar unit may be a monomer or oligomer of a hexose sugar. The structure of hexose sugars closely resemble the structure of starch-based adhesive oligomers, and the presence of a sugar unit on the additives of such embodiments may allow the chemical composition to become integrated into adhesive and confer the desired properties to the adhesive. More particular examples of hexose sugar monomers include D-glucose, D-allose, D-altrose, D-mannose, D-gulose, D-idose, D-galactose, and D-talose. These hexose sugars may also be in the form of oligomers either as a "pure" oligomer including a single species of hexose sugar, or the hexose sugars may be provided as a mixture of hexose sugars including D-glucose, D-allose, D-altrose, D-mannose, D-gulose, D-idose, D-galactose, and D-talose. Where the sugar unit is an oligomer of a hexose sugar, the hexose sugars are linked together by either $\alpha$-(1,4) or $\alpha$-(1,6) glycosidic bonds In an embodiment the additive is comprised of several molecular functional units conferring increased solubility and antimicrobial properties to the adhesive coupled with a sugar unit. In this embodiment, the molecular functional units and the sugar unit are colvalently linked via a linker molecule to form the additive.

In an embodiment, the additive is a molecule that includes three functional units: a sugar unit, a phenol or polyphenol side chain, and a Frechet-type poly (aryl ether) dendron. The parts are covalently bound together, and form an additive that sterically and chemically modifies starch-based adhesives, such as dextrin adhesives, to prevent otherwise uncontrolled levels of bonding between starch units of the adhesive. In this manner, the additive becomes an integral and interstitial unit in the final cured adhesive. The additive imparts new or altered properties to the modified cured adhesive, such as reduced brittleness, increased pliability and flexibility, antimicrobial properties, and other desirable properties absent in unmodified cured samples of the adhesive. The additive can be added in relatively small volume to volume amounts to starch-based dextrin adhesive stocks.

In another embodiment, the additive is a molecule that includes a dendron, a sugar unit bound to the dendron, and an antimicrobial agent bound to the dendron.

Methods of Preparation

Some embodiments are directed to methods for preparing the additives described above. Such additives can be synthesized by any method resulting in the covalent linkage of one or more molecular functional units and, in some cases, a sugar unit to a linker molecule such that the complete additive includes a single compound having covalently linked molecular functional groups that confer the desired properties to a starch-based adhesive. For example in some embodiments, additives such as those described above can be synthesized by a series of successive Mitsunobu coupling reactions. In such embodiments, a linker molecule such as 1,3,5-tris(bromomethyl)benzene can be covalently coupled to of either an alcohol terminated dendron or a propargyl alcohol via a Mitsunobu reaction in a first step to provide a first intermediate. In a second step, an anti-microbial agent may then be coupled to the first intermediate to provide anti-microbial activity to the additive. In some embodiments, a hexose sugar unit can be coupled to the linker molecule in a third step to facilitate insertion of the additive into the adhesive macromolecular structure. Of course, the order of coupling reactions can be arranged in any way. For example, an anti-microbial agent can be coupled to the linker in a first step, and a dendritic polymer can be coupled to the linker in a second step.

In other embodiments, additives can be synthesized using "click" chemistry to connect the dendron, antimicrobial agent, and, in some embodiments, a sugar unit to a linker molecule. The process for synthesizing an additive by this type of methodology is simple and results in high yields. For example, a 1,3,5-tris(bromomethyl)benzene linker 2 can be modified to replace bromines with an azide group and an alkyne group at one position on the linker.

A particular example is provided below. As illustrated in the first panel showing a first step in a "click" chemistry method for preparing a multi-functional additive, a dendron 1 can be reacted with 1,3,5-tris(bromomethyl)benzene (2) in the presence of a strong base such as sodium hydride and to form a dendron-linker intermediate 3.

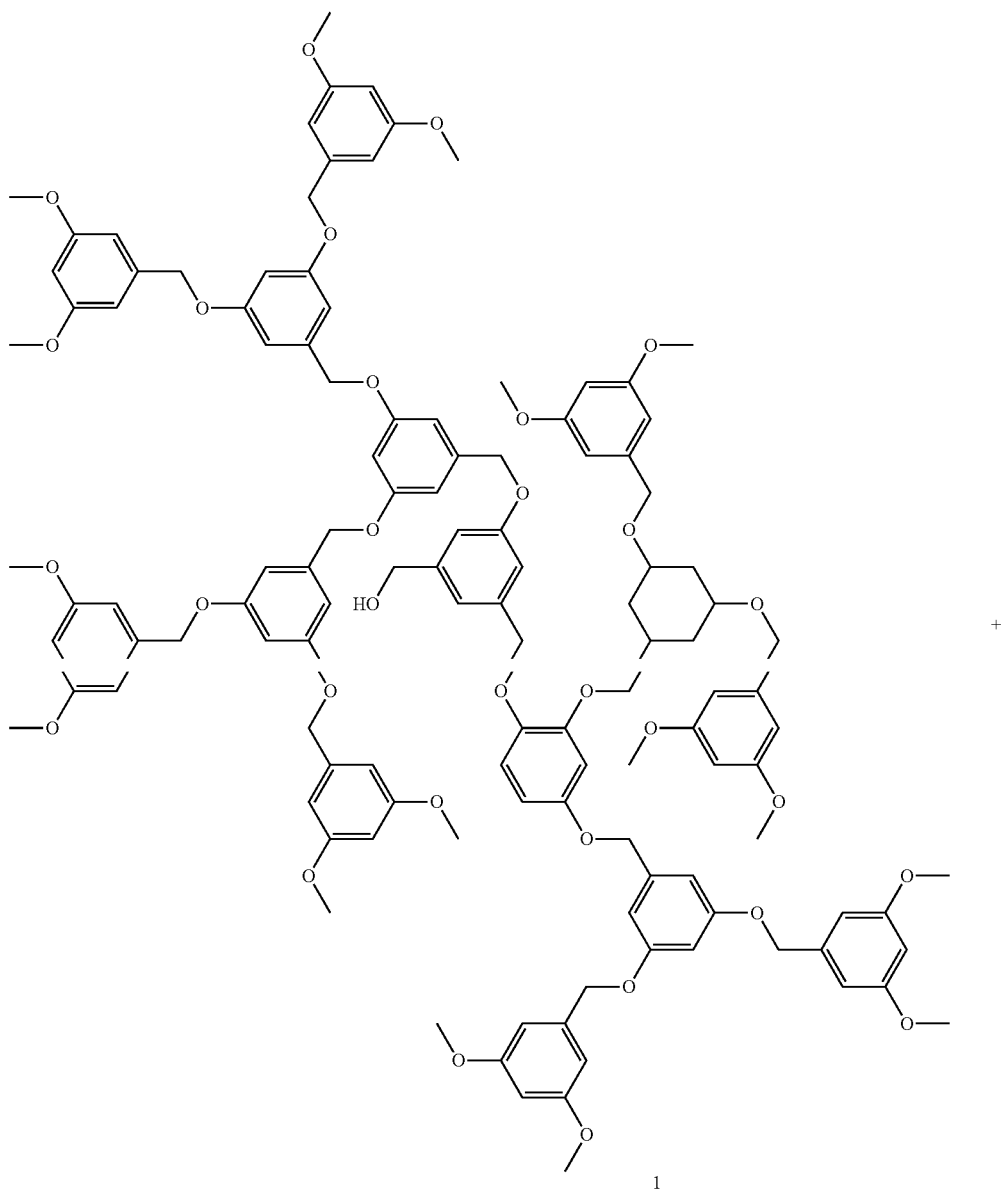

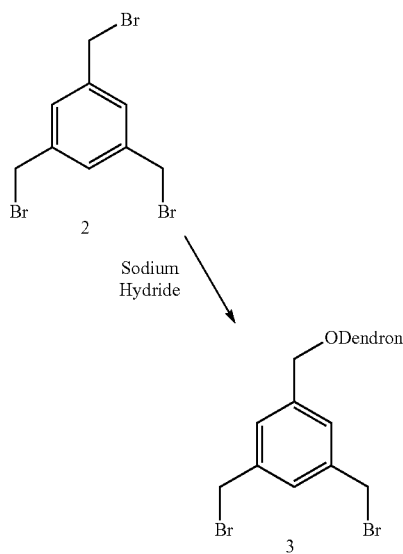

In a second step illustrated in the second panel, an antimicrobial agent, such as a derivative of pyrogallol-4-carboxylic acid salt 5 can be coupled to the linker-dendron intermediate 3 by a two step process. First, the linker-dendron intermediate 3 is reacted with propargyl alcohol, and a base, with a tetrahydrofuran (THF) serving as a solvent for the reaction to form a second linker-dendron intermediate 4 having an alkyne at one or more reactive groups. This second intermediate 4 is then reacted with an antimicrobial agent 5 in the presence of an organic solvent such as dimethylformamide (DMF) at a temperature range of 60-90° C. to create an additive 6 having an anti-microbial agent tethered to a dendron through a molecular linker.

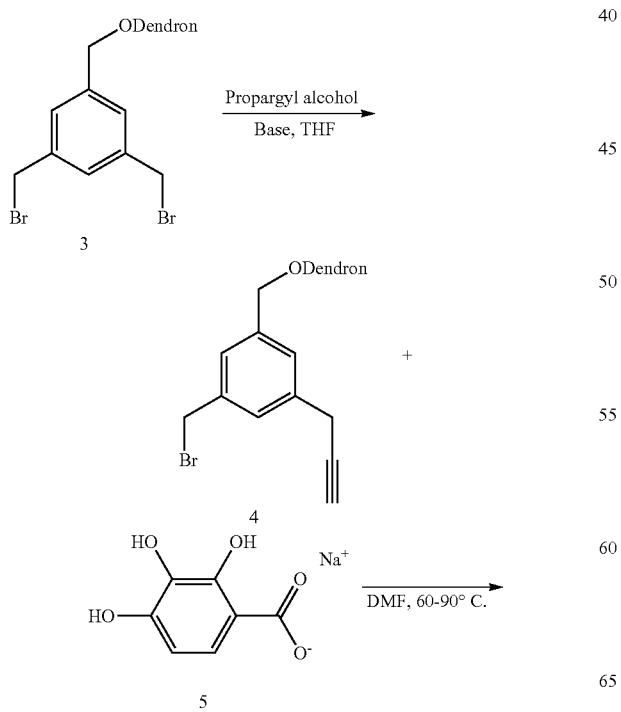

In some embodiments, a sugar group can be added to the additive 6. As illustrated in panel 3, the additive anti-microbial and dendron containing additive can be combined with a hexose sugar 7 in the presence of a catalyst such as a copper (II) catalyst and ascorbic acid and an organic solvent or water to couple the sugar to the additive followed by a hydrogenation reaction to form the complete additive 8.

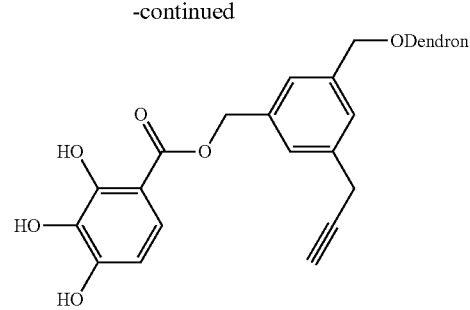

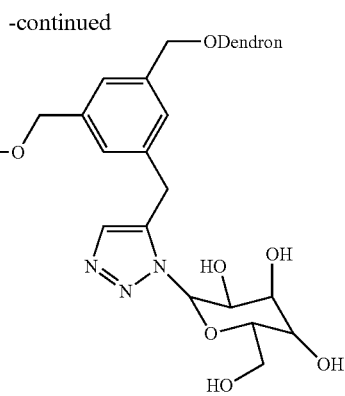

7

In some embodiments, a sugar group can be added to the additive 6. As illustrated in panel 3, the additive anti-microbial and dendron containing additive can be combined with a hexose sugar azide in the presence of a catalyst such as a copper (II) catalyst and ascorbic acid and an organic solvent or water to couple the sugar to the additive followed by a hydrogenation reaction to form the complete additive 7.

Starch-based dextrin adhesives are a major component of the paper and packaging industries. These adhesives are readily available, inexpensive, and easy to apply in the form of a water-based solution. They have numerous advantages over other types of adhesives including having a low production cost, providing solid adhesion to porous surfaces and oil insolubility, and being readily available, non-toxic and biodegradable. The manufacture of a generic starch adhesive typically begins by heating the starch in water, which bursts open the starch granules held together by internal hydrogen bonds. This forms a paste, which is used as the adhesive. Normally, above 15% starch solids contents, this cooked paste will form an insoluble rubbery mass upon cooling; however, with the proposed additive, much higher loading concentrations are possible. Higher solids concentrations are desirable as currently, the usefulness of dextrin-based adhesives is limited by a maximum solids concentration of approximately 25% w/v. High solids concentrations are related to the strength of the adhesive. As such, dextrin based adhesives form an extended network of inter- and intramolecular hydrogen bonds that are largely responsible for conferring strength to the adhesive. It is believed that the higher the solids concentration in the adhesive the higher the adhesive power of the adhesive. It is therefore desirable to achieve maximum solids concentrations ranging from for example 1-25% w/v, 25-50% w/v, 50-75% w/v and 75-100% w/v in a given volume of water. in some embodiments maximum solids concentrations will be in excess of 99% w/v, 98% w/v, 97% w/v, 96% w/v, 95% w/v, 90% w/v, 80% w/v, 70% w/v, 60% w/v, 50% w/v, 40% w/v, 30% w/v and 25% w/v. In some embodiments, the additive will confer to the adhesive in a water solvent carrier, a solids concentration of the modified starch-based adhesive in the water solvent carrier is greater than 25% w/v, 30% w/v, 40% w/v, 50% w/v, 60% w/v, 70% w/v, 80% w/v, 90% w/v, 95% w/v, 96% w/v, 97% w/v, 98% w/v and 99% w/v.

Dextrin adhesives in particular are commonly prepared by heating corn starch in the presence of acid. As mentioned above, British gums are roasted to around 170° C. for 24 hours, but suffer from low water solubility. For British gums, the maximum usable solids content is about 25%. In some embodiments, a multi-functional additive such as those described above can be added to a powdered-dextrin adhesive while the dextrin is still in the liquid (water) phase. Starch-based dextrin adhesives cure by loss of moisture. Upon evaporation of the solvent, which "cures" the adhesive, the additive can act as an internal plasticizer, held in place by its sugar moiety. The dendron confers sufficient steric bulk to disrupt the insoluble crystalline network of hydrogen bonds, and the antimicrobial agent controls the formation of microbial organisms over the lifetime of the adhesive.

In an embodiment, the additives described herein allow for the preparation of a "super-high-solid" dextrin-water adhesive, which decreases both shipping volume/cost as well as the required curing time since less water is required to evaporate. The resulting adhesive retains its strong adhesive character, is flexible, and is resistant microbial colonization.

In an embodiment, an additive is added to a powdered water-soluble adhesive prior to addition of water. The presence of the additive will increase the amount of powdered adhesive that can be dissolved in a particular amount of water and while retaining the adhesives desirable properties and providing antimicrobial properties to the cured adhesive.

In another embodiment, an additive is added to a powdered water-soluble adhesive after the addition of water so when the adhesive is in the liquid phase but prior to curing. The presence of the additive will increase the amount of powdered adhesive that can be dissolved in a particular amount of water while retaining the adhesives desirable properties and providing antimicrobial properties to the cured adhesive.

In another embodiment, an additive is added to water prior to the addition of a powdered water-soluble adhesive. The resulting mixture of additive and adhesive is in the liquid phase but prior to curing. The presence of the additive will increase the amount of powdered adhesive that can be dissolved in a particular amount of water while retaining the adhesives' desirable properties and providing antimicrobial properties to the cured adhesive.

The various preparation methods can further comprise heating the mixture of additive, adhesive, and water. In certain embodiments, the heating step is applied as needed to ensure complete mixing of the additive and adhesive. The heating step can be performed at generally any temperature. Example temperatures and ranges can include 20° C.-50° C., 50° C.-75° C. and 20° C.-75° C. In some embodiments, temperature ranges will be lower than the boiling point of water and lower than temperatures resulting in decomposition of organic solvents present. The heating step can be performed for generally any length of time. Example times and ranges can include 0-1 hours, 1-2 hours, 2-4 hours, 4-6 hours and 1-6 hours. The heating step can be performed until complete mixing of the adhesive and additive is achieved. The various methods can further comprise cooling the mixture after the heating step. In yet other embodiments, the heating and cooling steps are accompanied by physical mixing of the additive and adhesive mixtures. In an additional embodiment physical mixing of the additive and adhesive mixtures is performed in the absence of a heating or cooling step.

In yet another embodiment, the addition of an additive to an adhesive will increase the solids content of a particular adhesive water mixture to an amount above that which is achievable without the additive. For example, for British gums, the maximum usable solids content is about 25% in the absence of an additive but would be increased in the presence of an additive so that the net amount of powdered adhesive that can be dissolved in water. Specific examples of the maximum usable solids content are expected to be 50-75% in the presence of the additive. In some embodiments, the desired solids content will depend of the intended use of the adhesive. One skilled in the art will be able to determine the optimal solids content of an adhesive-additive mixture to meet usage requirements. Generally, the higher the solids content, the thicker and more viscous the adhesive-additive mixture become, and the stronger the cured adhesive will be.

In some embodiments the combination of the additive with a starch-based adhesive to form a modified starch-based adhesive, the resulting modified starch-based adhesive has a water solubility of about 101% to about 200% of the same starch-based adhesive in the absence of the additive.

Methods of Using Adhesives

A further embodiment includes using an adhesive composition comprising the adhesive and an additive composition to adhere a material to another material or to itself where the cured adhesive is resistant to microbial colonization by fungi, mold, and bacteria. Examples of such material include wood, paper, textile, leather, plastic, or cardboard.

The methods can comprise providing at least one material, applying the adhesive composition to the material, and adhering the material. The method can further comprise curing the adhesive composition. In one embodiment, the method comprises adhering a first portion of a first material to a second portion of the same first material. In an alternative embodiment, the method comprises adhering a first material to a second material. In some embodiments, the method can comprise applying the adhesive composition to the first portion of the first material and the second portion of the first material prior to adhering the first portion and the second portion. In some embodiments, the method can comprise applying the adhesive composition to both the first material and the second material prior to adhering the first material to the second material.

The resistance to adverse factors such as microbial colonization by fungi, mold, and bacteria can be measured relative to the same cured adhesive prepared from a similar adhesive composition but lacking the additive composition. The percent resistance can generally be any percent resistance. Examples of percent resistance include at least about 10%, at least about 20%, at least about 30%, at least about 40%, at least about 50%, at least about 60%, at least about 70%, at least about 80%, at least about 90%, at least about 95%, at least about 96%, at least about 97%, at least about 98%, at least about 99%, and ranges between any two of these values. In an idealized embodiment, the percent resistance is 100%, that is, the cured adhesive is completely resistant to the adverse factor.

EXAMPLES

Example 1

Synthesis of a Starch-Based Dextrin Adhesive Additive by "Click" Chemistry

A multi-functional additive can be prepared using multi-step coupling reactions. In a first step, a first, second, third, or fourth generation polybenzylether dendron (0.48 mmol) can be dissolved in 10 mL of diethyl ether, followed by addition of 1,3,5-tris(bromomethyl)benzene (0.41 g, 2.9 mmol). Neat Calcium hydride (19.71 mg) can be added to this mixture, and the mixture can be stirred for 24 hours at room temperature. The solvent can then be removed using a rotary evaporator, and the remaining compound can be washed to remove residual 1,3,5-tris(bromomethyl)benzene by dissolving the compound in water and washing with chloroform.

In a second coupling step, the compound produced in the first step can be dissolved in tetrahydrofuran (THF, 10 mL), and propargyl alcohol (0.0005 mol) followed by addition of sodium hydride (10 mL 50% solution in water). This solution can be stirred for 24 hours at room temperature. The resulting compound can be isolated by evaporating the solvent in a rotary evaporator. The compound can then by dissolved in dimethylformamide (DMF, 10 mL), and gallic acid sodium salt (10.0 mmol) can be added to this solution. The mixture can then be heated to 60° C. to 90° C., and stirred for 24 hours. The resulting compound should include polybenzylether dendrimers tethered to gallic acid by the 1,3,5-tris(bromomethyl)benzene linker. This compound can be used as an additive.

In a third coupling step, a sugar moiety can also be added to the additive. This can be accomplished by dissolving the additive resulting from the second coupling step in water and adding D-glucose (10.0 mmol), copper sulphate ($CuSO_4$ 0.16 mM), tertbutanol (t-BuOH, 8 mM), and ascorbic acid (5.0 mM). The resulting solution can be heated to 40° C., and stirred for 12 hours. After reacting the product can be hydrogenated by adding Raney nickel catalyst (2-6 g, pore size 50μ and surface area 90 $m^2$/g in 50% water, nickel content 75.1%) to the reaction mixture to form the reaction slurry, heating the slurry to 45° C., and feeding hydrogen gas through the slurry at a flow rate of 1.86 liter/minute using a perforated glass bulb tube to keep the slurry in considerable agitation during the reaction. The resulting additive having a polybenzylether dendrimers tethered to gallic acid and D-glucose by the 1,3,5 methyl benzene 1,3,5-tris(bromomethyl)benzene linker can be isolated by evaporating the solvents in a rotary evaporator, dissolving the compound in water, and washing with chloroform several times until the desired purity is reached. The solvent can be removed and the additive can be dried and stored as a powder.

Example 2

Synthesis of a Starch-Based Dextrin Adhesive Additive by "Click" Chemistry with an Alkyne Linker A multi-functional additive can be prepared using multi-step coupling reactions. In a first step, a first, second, third, or fourth generation polybenzylether dendron coupled to a bromomethyl group is reacted with 1,3,5-trimethyl benzene to form an alkyne-linker-dendron intermediate (1). Neat sodium hydride can be added to this mixture, and the mixture can be stirred for 24 hours at room temperature. The solvent can then be removed using a rotary evaporator, and the remaining compound can be washed to remove residual 1,3,5-trimethyl benzene by dissolving the compound in water and washing with chloroform.

In a second step, intermediate 1, an antimicrobial agent 2, prepared by treatment of gallic acid with trimethylchlorosilane (TMSCI) and then oxalyl chloride, can be coupled to the alkyne-linker-dendron intermediate 1 by a two step process. First, the linker-dendron intermediate 1 is reacted with the antimicrobial agent 2, in the presence of neat sodium hydride with a tetrahydrofuran (THF) serving as a solvent for the reaction followed by reaction with dilute hydrochloric acid to form a second linker-dendron intermediate 3 having an alkyne at one or more reactive groups and an anti-microbial agent tethered to the alkyne-linker-dendron intermediate. Intermediate 3 is reacted with a sugar azide moiety in the presence of copper (II), ascorbic acid, tert-butanol, water followed by a hydrogenation to yield the completed additive 4.

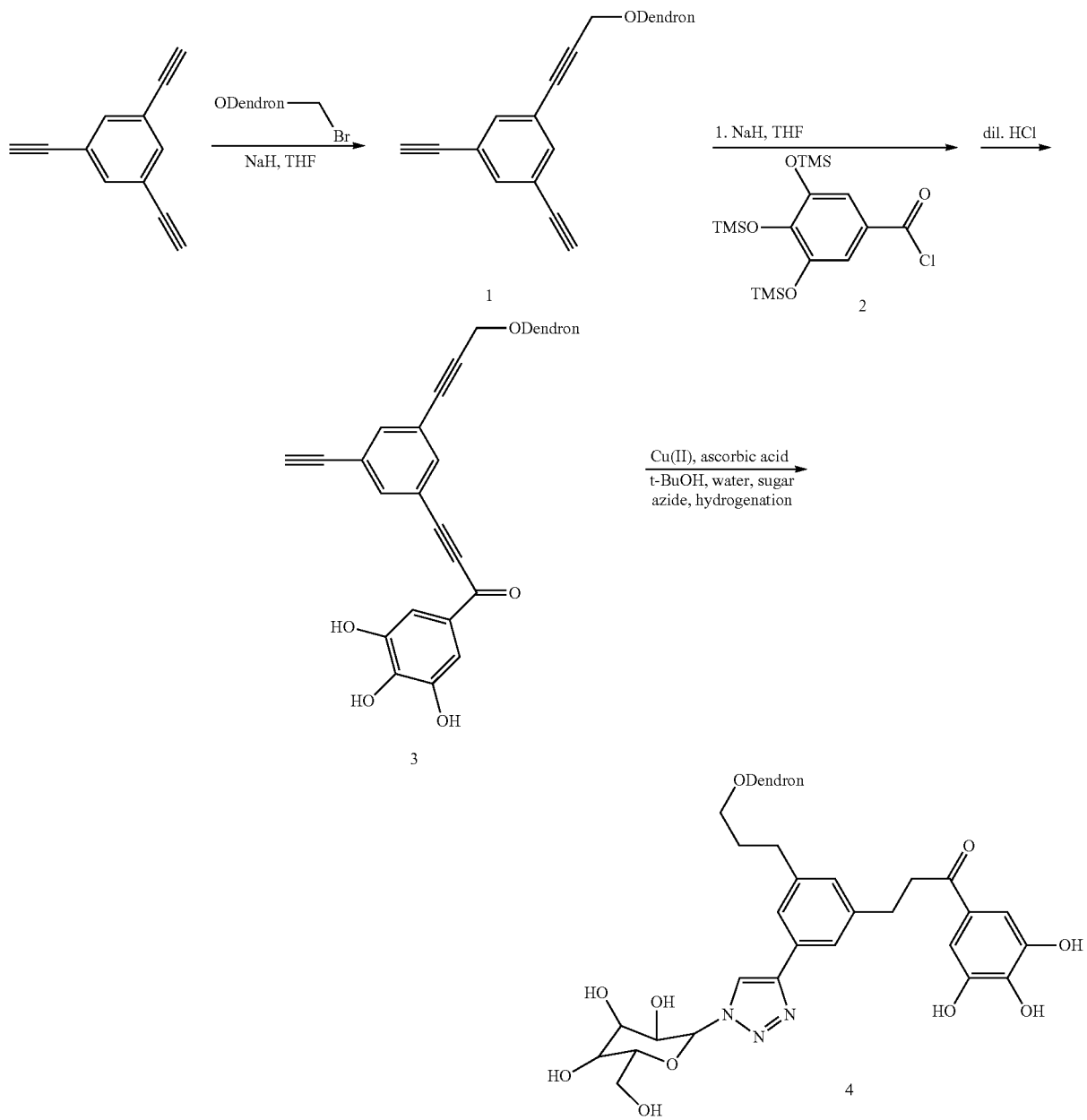

Example 3

Synthesis of a Starch-Based Dextrin Adhesive Additive by "Click" Chemistry with a Halide Linker A multi-functional additive can be prepared using multi-step coupling reactions. In a first step, 1,3,5-triodobenzene is reacted with 3 equivalents of trimethylsilylacetylene, 5% palladium(II) chloride triphenylphosphine, 5% copper (II) carboxylate, piperidines at 25° C. for 6 hours followed by reaction with potassium carbonate in methanol at 25° C. for 30 minutes to form 1,3,5-trimethyl benzene.

In a second step, a first, second, third, or fourth generation polybenzylether dendron coupled to a bromomethyl group is reacted with 1,3,5-trimethyl benzene to form an alkyne-linker-dendron intermediate (2). Neat sodium hydride can be added to this mixture, and the mixture can be stirred for 24 hours at room temperature. The solvent can then be removed using a rotary evaporator, and the remaining compound can be washed to remove residual 1,3,5-trimethyl benzene by dissolving the compound in water and washing with chloroform.

In a third step, intermediate 2, and an antimicrobial agent 3, prepared by treatment of gallic acid with trimethylchlorosilane (TMSCl) and then oxalyl chloride, can be coupled to the alkyne-linker-dendron intermediate 2 by a two step process. First, the linker-dendron intermediate 2 is reacted with the antimicrobial agent 3, in the presence of neat sodium hydride with a tetrahydrofuran (THF) serving as a solvent for the reaction followed by reaction with dilute hydrochloric acid to form a second linker-dendron intermediate 4 having an alkyne at one or more reactive groups and an anti-microbial agent tethered to the alkyne-linker-dendron intermediate.

Intermediate 4 is reacted with a sugar azide moiety in the presence of copper (II), ascorbic acid, tert-butanol, and water followed by a hydrogenation to yield the completed additive 5.
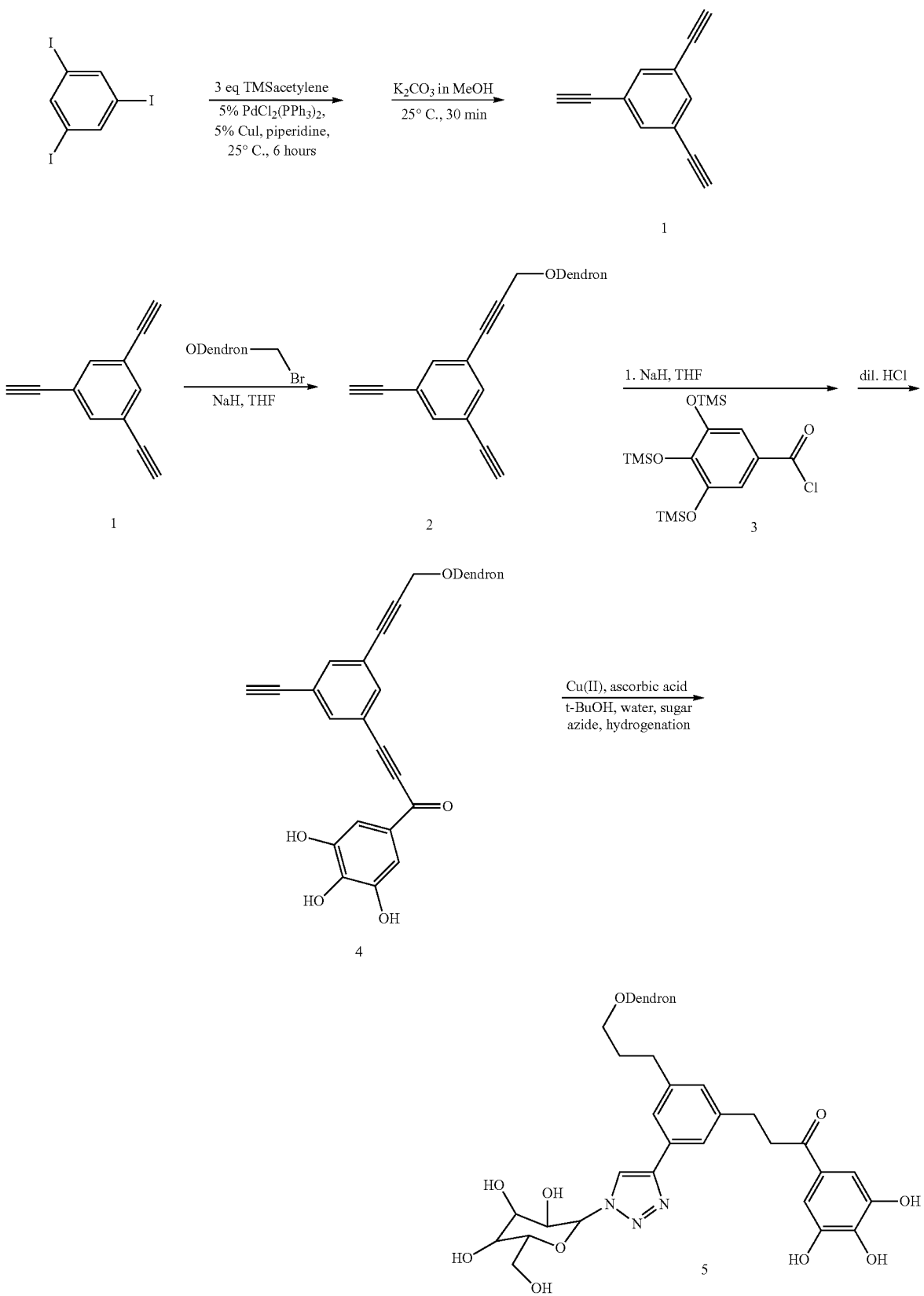

Example 4

Synthesis of a Starch-Based Dextrin Adhesive Additive by "Click" Chemistry with an Ester Linker A multi-functional additive can be prepared using multi-step coupling reactions. In a first step, a first, second, third, or fourth generation polybenzylether dendron coupled to a hydroxyl group is reacted with a benzene-1,3,5-tricarboxylic acid trimethyl ester to form an ester-linker-dendron intermediate (1). Neat sodium hydride can be added to this mixture, and the mixture can be stirred for 24 hours at room temperature. The solvent can then be removed using a rotary evaporator, and the remaining compound can be washed to remove residual benzene-1,3,5-tricarboxylic acid trimethyl ester by dissolving the compound in water and washing with chloroform.

In a second step, intermediate 1 and an antimicrobial agent 2, (potassium; 3,4,5-trihydroxy-benzoate), can be coupled to the ester-linker-dendron intermediate 1 by a two step process. First, the linker-dendron intermediate 1 is reacted with neat sodium hydride and a tetrahydrofuran (THF) serving as a solvent for the reaction followed by reaction with antimicrobial agent 2 in dimethylformamide (DMF) at 100° C. and then secondly, reacted with Pent-4-yn-1-ol in the presence of neat sodium hydride with a tetrahydrofuran (THF) serving as a solvent for the reaction to form a second linker-dendron intermediate 3 having an at one or more reactive groups and an anti-microbial agent (2) tethered to the ester-linker-dendron intermediate. Intermediate 3 is then reacted with a sugar azide moiety in the presence of copper (II), ascorbic acid, tert-butanol, and water followed by a hydrogenation to yield the completed additive 4.

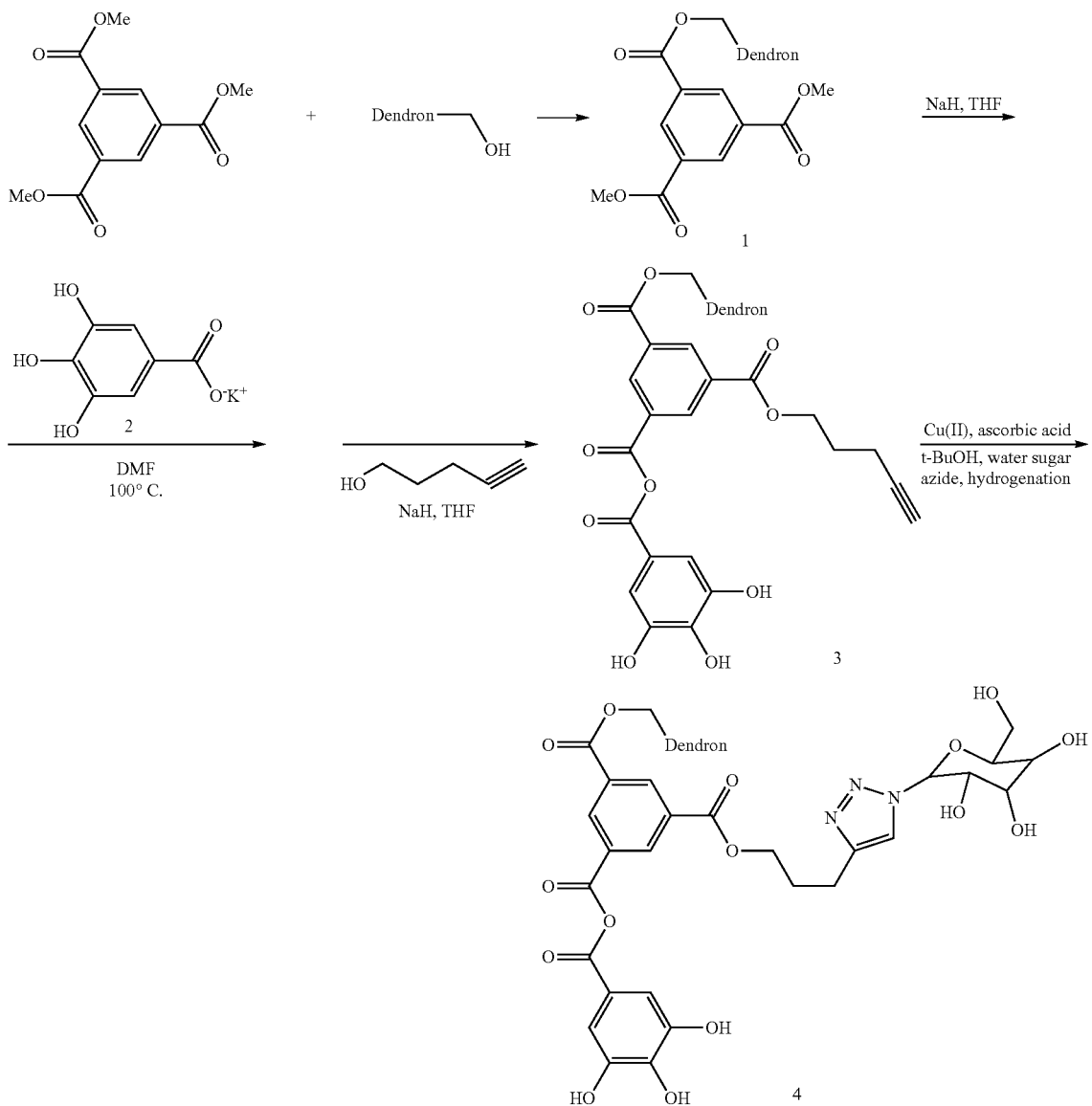

Example 5

Synthesis of a Starch-Based Dextrin Adhesive Additive by "Click" Chemistry with an Acid Chloride Linker A multi-functional additive can be prepared using multi-step coupling reactions. In a first step, a first, second, third, or fourth generation polybenzylether dendron coupled to a hydroxyl group is reacted at 25° C. in the presence of pyridine with a Benzoyl chloride to form an acid chloride-linker-dendron intermediate. This intermediate is then reacted at 25° C. in the presence of pyridine with an antimicrobial agent (1) with the general formula HO—(CH2)x-NR3X where R can be an alkyl group of variable length from 1 to 18 carbons, x can be any number between 2 and 18 and X can be any singly charged anion such as a chloride or bromide anion, followed by a reaction with propargyl alcohol at 25° C. in the presence of pyridine to form intermediate 2. Intermediate 2 is then reacted with a sugar azide moiety in the presence of copper (II), ascorbic acid, tert-butanol, and water followed by a hydrogenation to yield the completed additive 3.

Example 6

Synthesis of a Starch-Based Dextrin Adhesive Additive by "Click" Chemistry with an Aldehyde Linker A multi-functional additive can be prepared using multi-step coupling reactions. In a first step, a first, second, third, or fourth generation polybenzylether dendron coupled to an ethyl-phosphonic acid diethyl ester group with a 3,5-Dimethyl-benzaldehyde to form an aldehyde-linker-dendron intermediate (1) by mesylation of the dendron alcohol followed by treatment with sodium iodide and triethylphosphite at reflux.

Intermediate 1 is then reacted at 50° C. in the presence of neat sodium hydride and a tetrahydrofuran with an quaternary amine alcohol antimicrobial agent (2) with the general formula (EtO)2(O)P—(CH2)x-NR3X where R can be an alkyl group of variable length from 1 to 18 carbons, x can be any number between 2 and 18 and X can be any singly charged anion such as a chloride or bromide anion, by mesylation of

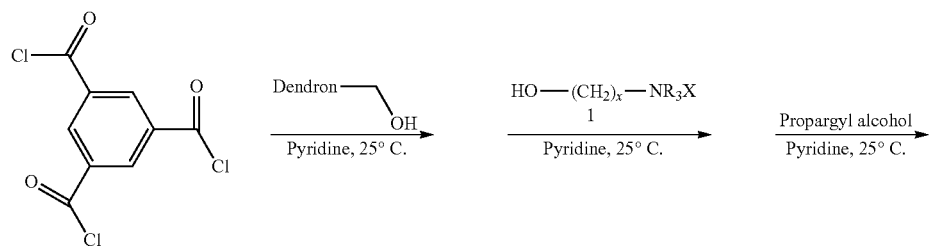

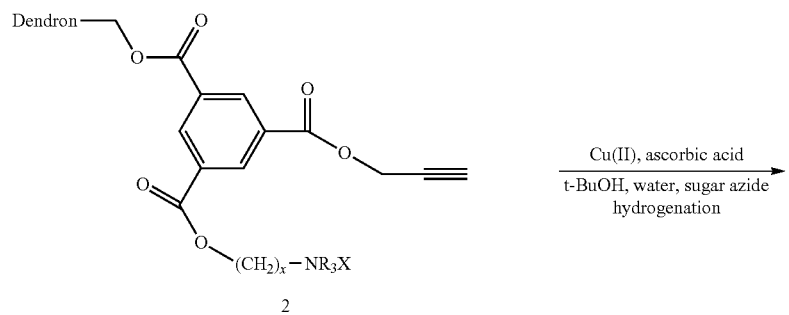

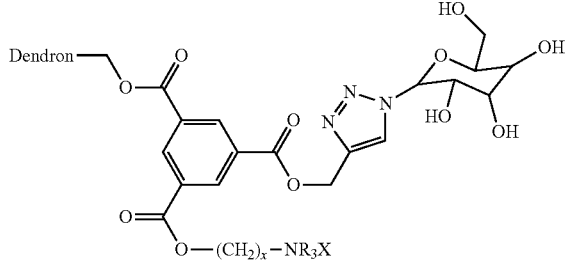

the quaternary amine alcohol followed by treatment with sodium iodide and tiethylphosphite at reflux. This is followed by a reaction with a hex-5-ynyl-phosphonic acid diethyl ester (3) at 50° C. in the presence of neat sodium hydride in a tetrahydrofuran solvent to form intermediate 4 by an Arbusov rearrangement of omega-terminated bromide with triethyl phosphate. Intermediate 4 is then reacted with a sugar azide moiety in the presence of copper (II), ascorbic acid, tert-butanol, and water followed by a hydrogenation to yield the completed additive 5.

The additive powder prepared as described in Example 1 (100 mg) can be added to a slurry including white dextrin (1000 g) in water (1 L) to create an adhesive mixture.

The additive powder prepared as described in example 1 (100 mg) can be added to water (1 L) followed by addition of white dextrin (1000 g) in water (1 L) to create an adhesive mixture.

In some embodiments, the mixture of water, adhesive and additive are mixed in cold water for about 30 minutes. In yet other embodiments, the mixture of water, adhesive and addi-

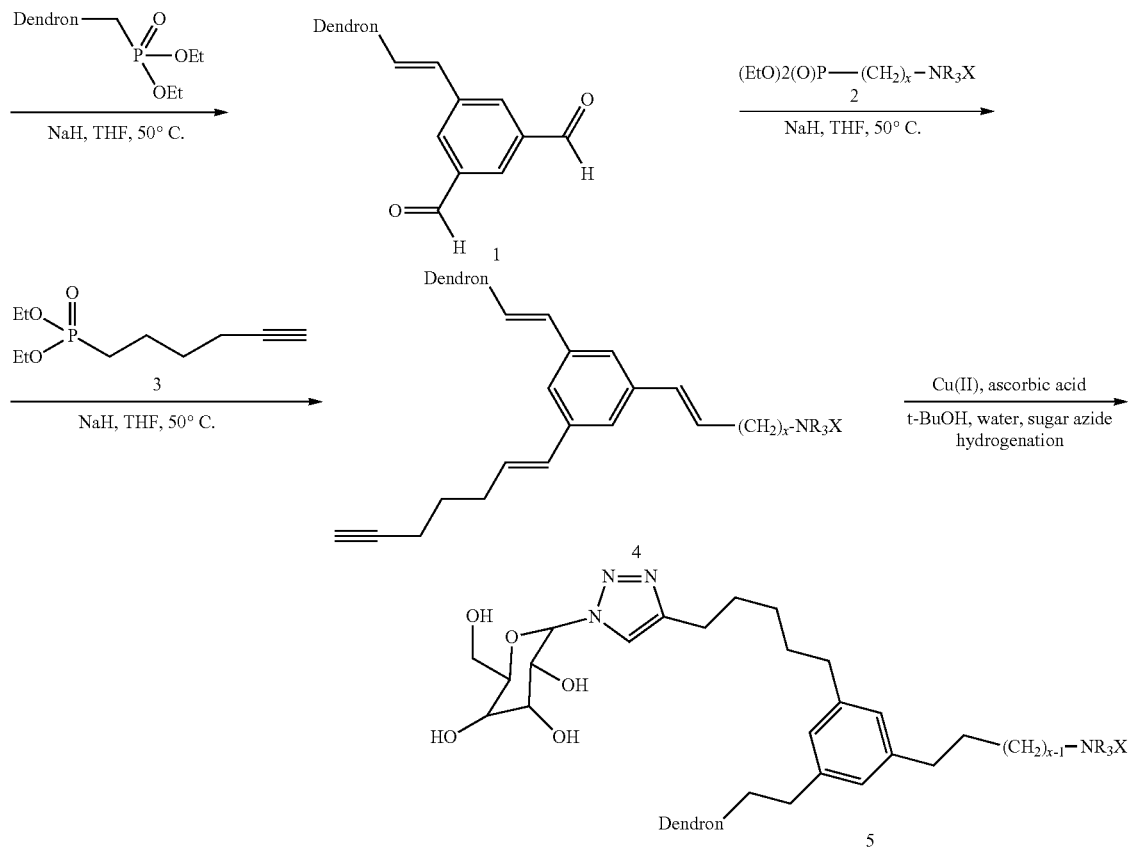

Example 7

Preparation of Adhesive-Additive Mixture

The additive powder prepared as described in Example 1 (0.5 mg) can be added to dry white dextrin (100 g), and water (1 L) can be added to this mixture to create an adhesive mixture.

The additive powder prepared as described in Example 1 (500 mg) can be added to a slurry including white dextrin (100 g) in water (1 L) to create an adhesive mixture.

The additive powder prepared as described in example 1 (500 mg) can be added to water (1 L) followed by addition of white dextrin (100 g) in water (1 L) to create an adhesive mixture.

The additive powder prepared as described in Example 1 (100 mg) can be added to dry white dextrin (1000 g), and water (1 L) can be added to this mixture to create an adhesive mixture.

tive is mixed and heated to a temperature exceeding 20° C. and subsequently cooled prior to curing.

Example 8

Use of an Adhesive-Additive Mixture in the Manufacture of Corrugated Cardboard Boxes The adhesives prepared as described in Example 2 can be used in the manufacture of corrugated cardboard blanks for use in making cardboard boxes. Corrugated cardboard blanks are produced in a continuous two-step operation consisting of corrugating a strip of cardboard by means of heated fluted rolls, applying the adhesive in Example 2 to the tips of the corrugations on one side, bringing a smooth cardboard liner in contact with the corrugations and forming a bond by providing pressure sufficient to hold the liner and corrugated paper in contact to form a single faced corrugated cardboard. In a second step, the adhesive of example 2 is applied to the tips of the corrugated cardboard that remain exposed followed by contacting the exposed corrugated tips to a second smooth cardboard liner and forming an adhesive bond by providing pressure sufficient to hold the liner and corrugated paper in contact. The result of this two step process is a stiff cardboard comprising two smooth outer cardboard surfaces bonded to an inner core of corrugated cardboard. The double-faced corrugated cardboard blank produced by this process can be used to form boxes whereby the stiff corrugated cardboard is folded over and adhered to another portion of the same stiff corrugated cardboard comprising a first, second, third, and fourth side wall panel, wherein the first and third side wall panels are in opposed relationship, and wherein the second and fourth side wall panels are in opposed relationship, the side wall panels defining an interior space of the box. The adhesive in example 2 can also be utilized to adhere portions of a cardboard box to one another. In some embodiments this can be achieved by the application of sufficient pressure so as to maintain portions of the folded cardboard blank in contact unless a bond is formed and adhesive has cured.

In some embodiments, the cardboard blank is produced as described above with the additional step of applying heat in conjunction with sufficient pressure to hold the liner and corrugated paper in place.

The resulting cardboard box benefits from the added features of the adhesive containing an additive. The features include greater, strength and resistance to microbial colonization on areas where adhesive is present.

Example 9

Use of an Adhesive-Additive Mixture in the Manufacture of Textile Products

The adhesives prepared as described in Example 2 can be used in the manufacture of textile products. Examples include clothing garments, household items, such as carpets and rugs, towels, curtains and sheets, furniture and automotive upholstery, and industrial belts and fire hoses. Textile products can be produced by the adhesion of separate pieces of non-woven fabric or by the adhesion of a portion of a piece of fabric to another portion of the same piece of fabric. Examples of non-woven fabrics include spunlace, spunbond, and blends of polyester, polypropylene, and/or polyethylene, as well as combinations thereof. The adhesive described in Example 2 can be used to adhere single or separate pieces of non-woven fabrics by a process of contacting the adhesive to the surface of fabric followed by contacting a second surface of either the same piece of textile or a separate piece of textile and applying sufficient pressure to hold the pieces of fabric in contact while the adhesive cures. The result of this process is two pieces of fabric bonded together with sufficient strength to withstand the stress of the products intended usage as well as resistance to colonization by microbial organisms at the sight of the bond.

In some embodiment, the textile product can be made as described above with the additional step of applying heat in conjunction with sufficient pressure to hold the pieces of textile in place.

Example 10

Comparison of Adhesive-Additive Mixture Against Adhesive Lacking Additive

The properties of a particular adhesive-additive mixture can be compared with those of adhesives in the absence of an additive by a number of standard testing methodologies including peel, tension, compression and sheer tests. These tests measure the strength of a cured adhesive and its ability to withstand a variety of stresses that can be encountered in its use. A peel test will measure the force required to separate to two adhered substrates, for example two pieces or fabric or two pieces of cardboard, in terms of the force, angle and time required to achieve separation of the adhesive from the substrates. A peel test will provide an indication of the level of stress required before a particular adhesive fails and separates from a substrate. Tension, compression and sheer tests allow for the characterization of adhesion provided by a particular adhesive and the forces required to cause separation of the adhesive from a substrate or separation of two substrates adhered together. These tests will permit a user to evaluate the differences in strength of an adhesive with and without an additive.

In addition, tests can be performed to analyze the characteristics of the adhesive in the presence of an additive while the adhesive is in the liquid stage. Such tests may measure viscosity and solubility of the adhesive. The ability of an adhesive additive to increase viscosity of an adhesive in the liquid phase can be measured by observing the rate of flow of a sample of an adhesive from one container to another positioned below the first container such that adhesive will flow in a constant stream under the force of gravity. The viscosity of an adhesive containing an additive can be compared directly to the same adhesive in the absence of an additive while both adhesives are in the liquid phase. More sophisticated measurement devices exist to obtain a quantitative comparison of the viscosity of an adhesive in the liquid phase. These include falling and oscillatory piston viscometers, Stabinger and Stormert rotational viscometers which can be used if a particular liquid-phase adhesive is characterized a Newtonian fluid. Where the adhesive in liquid phase represents a non-Newtonian fluid then instruments including rheometers and plastometers can be used to measure viscosity of a particular adhesive.

Increased resistance of an adhesive preparation to attack by bacteria yeast and fungi can be measured by exposing a sterile adhesive to selected microbes and monitoring the adhesives return to sterility. In addition, the presence of microbes on the surface or within a particular adhesive can be monitored by contacting the adhesive with a letheen agar plate and monitoring microbe growth on the agar plate. This can be done after specifically infecting the adhesive with a selected microbe or contacting the adhesive with the letheen agar plate after exposure to conditions that would simulate the additives sue. These methods would allow for testing of adhesives with and without additives in both the liquid phase and after curing.

Additional tests can be performed to measure the performance of an adhesive containing an additive compared with the same adhesive in the absence of an additive. Such tests might include exposure of the cured adhesive to a range of temperatures and pressures to mimic the conditions in which the adhesive would be used. Another characteristic that can be readily measured is the performance of an adhesive containing an additive after varying amounts of exposure to sunlight. These conditions can be replicated under laboratory conditions by exposing the cured adhesive to varying amounts of ultraviolet light for a variety of durations and then performing the tests described above. As with the tests described above, the potential benefit of an additive to a particular feature of an adhesive can be quantified by comparing the adhesive in the presence of an additive to the same adhesive in the absence of the additive.

Solubility of a water-based adhesive is an important feature that can be enhanced in the presence of an additive. To measure solubility of an adhesive powder in water, light or laser refraction can be used to measure the presence of particles of un-dissolved adhesive. A specified amount of adhesive can be added to a measured amount of water and the relative light or laser refraction can be measured as a surrogate for solubility of the powdered adhesive. This method permits the comparison of the solubility of a particular adhesive in the presence or absence of an additive. An alternative method for measuring the solubility of measured amounts of an adhesive with and without an additive is to measure adhesive sedimentation after application of a mild centrifugal force to the adhesive-water mixture. It is expected that higher levels of sedimentation are correlated with lower levels of solubility of the adhesive.

Furthermore, not only can the tests described above provide a quantitative measure of the benefit conferred to an adhesive by a particular additive, these tests can also be used to determine the amounts of a particular additive that will be needed to confer or enhance the desired property in an adhesive.

In the present disclosure, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the FIGURE, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a" system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 substituents refers to groups having 1, 2, or 3 substituents. Similarly, a group having 1-5 substituents refers to groups having 1, 2, 3, 4, or 5 substituents, and so forth.

What is claimed is:

1. A modified starch-based adhesive comprising a starch-based adhesive and an additive, the additive comprising a dendron, a sugar unit bound to the dendron, and an antimicrobial agent bound to the dendron.

2. The modified starch-based adhesive of claim 1, wherein the antimicrobial agent comprises at least one of a phenol, a quaternary ammonium salt, 4-hydroxybenzoic acid, a hydroxytyrosol, alkyl esters of gallic acid, and combinations thereof.

3. The modified starch-based adhesive of claim 2, the phenol is selected from a polyphenol, gallic acid and a combination thereof.

4. The modified starch-based adhesive of claim 2, the quaternary ammonium salt is selected from benzalkonium chloride, benzethonium chloride, methylbenzethonium chloride, cetalkonium chloride, cetylpyridinium chloride, cetrimonium, cetrimide, dofanium chloride, tetraethylammonium bromide, didecyldimethylammonium chloride, domiphen bromide and a combination thereof.

5. The modified starch-based adhesive of claim 1, wherein the antimicrobial agent comprises a quaternary ammonium salt having a structure of the formula O-alkyl-NR$^1$R$^2$R$^3$X, wherein R$^1$-R$^3$ are alkyl chains, and wherein X is a counterion.

6. The modified starch-based adhesive of claim 5 wherein the counterion comprises a chloride.

7. The modified starch-based adhesive of claim 1, wherein the dendron is a Frechet-type poly (aryl ether) dendron.

8. The modified starch-based adhesive of claim 7 wherein the dendron comprises a generation 3 Frechet-type poly(aryl ether) dendron, a generation 4 Frechet-type poly(aryl ether) dendron, or a generation 5 Frechet-type poly(aryl ether) dendron.

9. The modified starch-based adhesive of claim 1, wherein the sugar unit is an oligometer of a hexose sugar, linked together by either α-(1,4) or α-(1,6) glycosidic bonds.

10. The modified starch-based adhesive of claim 1, wherein, upon combination of the additive with a starch-based adhesive to form a modified starch-based adhesive, the modified starch-based adhesive has a water solubility of about 101% to about 200% of the same starch-based adhesive in the absence of the additive.

11. The modified starch-based adhesive of claim 1, wherein upon combination of the additive with a starch-based adhesive to form a modified starch-based adhesive, the modified starch-based adhesive becomes more resistant to growth of at least one of mold, fungus, bacteria, and combinations thereof than a sample of the same starch-based adhesive in the absence of the additive.

12. The modified starch-based adhesive of claim 1, wherein upon combination of the additive with a starch-based adhesive to form a modified starch-based adhesive, and upon curing, the modified starch-based adhesive is more pliable, more resistant to chipping, more resistant to cracking, or more resistant to microbial growth than a cured sample of the same starch-based adhesive in the absence of the starch-based adhesive.

13. The modified starch-based adhesive of claim 1, wherein the additive comprises the formula:

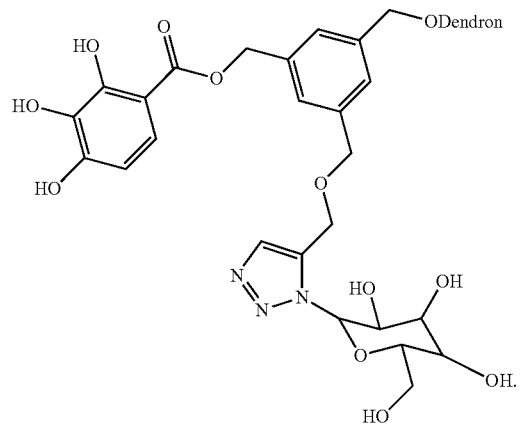

14. The modified starch-based adhesive of claim 1, wherein the dendron comprises a linker molecule covalently bonded to the dendron.

15. The modified starch-based adhesive of claim 14, wherein the linker molecule is 1,3,5, tris bromomethyl benzene.

16. The modified starch-based adhesive of claim 1, further comprising a water solvent carrier, wherein a solids concentration of the modified starch-based adhesive in the water solvent carrier is greater than 25% w/v.

17. The modified starch-based adhesive of claim 1, wherein the starch-based adhesive is a dextrin adhesive.

18. The modified starch-based adhesive of claim 9, wherein the hexose sugar is selected from D-glucose, D-allose, D-altrose, D-mannose, D-gulose, D-idose, D-galactose, D-talose and combinations thereof.

19. The modified starch-based adhesive of claim 1, wherein the additive comprises the formula:

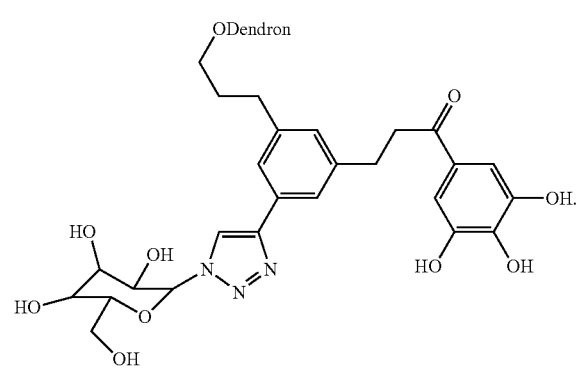

20. The modified starch-based adhesive of claim 1, wherein the additive comprises the formula:

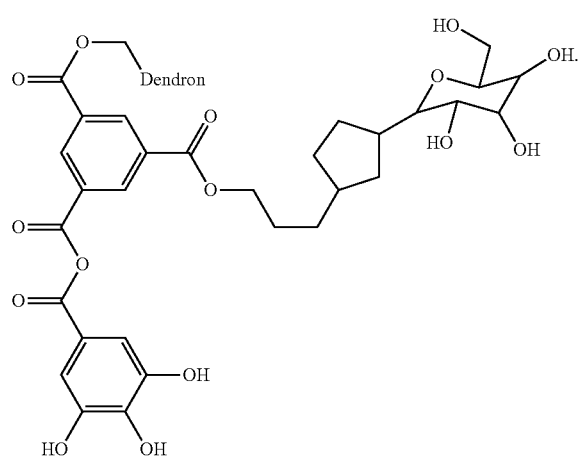

21. The modified starch-based adhesive of claim 14, wherein the additive comprises the formula:

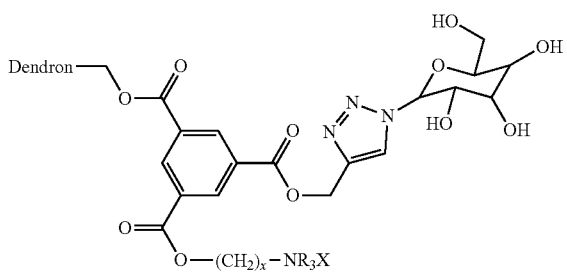

wherein x is an integer between 2 and 18, R is an alkyl group of variable length from 1 to 18 carbons and wherein X is a counterion selected from chloride and bromide.

22. The modified starch-based adhesive of claim 1, wherein the additive comprises the formula:

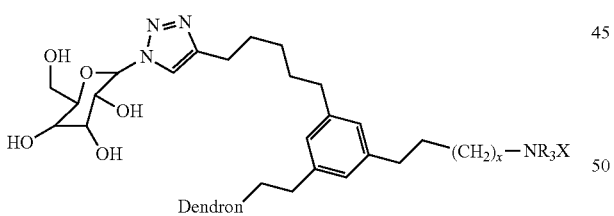

wherein x is an integer between 2 and 18, R is an alkyl group of variable length from 1 to 18 carbons and wherein X is a counterion selected from chloride and bromide.

23. A method of forming a modified a starch-based adhesive, the method comprising addition of an additive to a starch-based adhesive wherein the additive comprises a dendron, a sugar unit bound to the dendron, and antimicrobial agent bound to the dendron.

24. The method of claim 23, wherein the antimicrobial agent comprises at least one of a phenol, a quaternary ammonium salt, 4-hydroxybenzoic acid, a hydroxytyrosol, alkyl esters of gallic acid, and combinations thereof.

25. The method of claim 23, wherein the antimicrobial agent comprises a quaternary ammonium salt having a structure of the formula O-alkyl-$NR^1R^2R^3X$, wherein $R^1$-$R^3$ are alkyl chains, and wherein X is a counterion.

26. The method of claim 23, wherein the dendron is a Frechet-type poly (aryl ether) dendron.

27. The method of claim 23, wherein the sugar unit is an oligomer of a hexose sugar, linked together by either α-(1,4) or α-(1,6) glycosidic bonds.

28. The method of claim 23, wherein, upon combination of the additive with a starch-based adhesive to form a modified starch-based adhesive, the modified starch-based adhesive has a water solubility of about 101% to about 200% of the same starch-based adhesive in the absence of the additive.

29. The method of claim 23, wherein upon combination of the additive with a starch-based adhesive to form a modified starch-based adhesive, the modified starch-based adhesive becomes more resistant to growth of at least one of mold, fungus, bacteria, and combinations thereof than a sample of the starch-based adhesive in the absence of the additive.

30. The method of claim 23, wherein upon combination of the additive with a starch-based adhesive to form a modified starch-based adhesive, and upon curing, the modified starch-based adhesive is more pliable, more resistant to chipping, more resistant to cracking, or more resistant to mocrobial growth than a cured sample of the starch-based adhesive in the absence of the additive.

31. The method of claim 23 whereby the dendron additive comprises the formula:

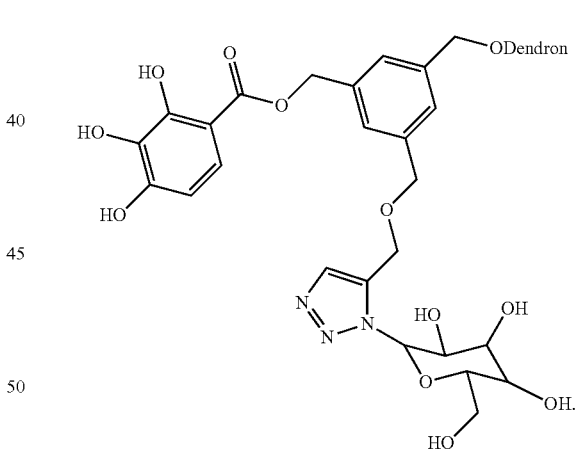

32. The method of claim 23, further comprising adding a water solvent carrier, wherein a solids concentration of the modified starch-based adhesive in the water solvent carrier is greater than 25% w/v.

* * * * *

UNITED STATES PATENT AND TRADEMARK OFFICE
CERTIFICATE OF CORRECTION

PATENT NO. : 8,382,889 B1
APPLICATION NO. : 13/389582
DATED : February 26, 2013
INVENTOR(S) : Brizius It is certified that error appears in the above-identified patent and that said Letters Patent is hereby corrected as shown below:

On the Title Page, in Item (56), under "OTHER PUBLICATIONS", in Column 2, Line 8, delete "Carbohydr Res" and insert -- Carbohydr. Res. --, therefor.

On the Title Page, in Item (56), under "OTHER PUBLICATIONS", in Column 2, Line 10, delete "2,3,4-Trihdroxybenzoic" and insert -- 2,3,4-Trihydroxybenzoic --, therefor.

On the Title Page, in Item (56), under "OTHER PUBLICATIONS", in Column 2, Line 14, delete "chemistry".," and insert -- chemistry", --, therefor.

On the Title Page, in Item (56), under "OTHER PUBLICATIONS", in Column 2, Line 20, delete "Pharm Res" and insert -- Pharm. Res. --, therefor.

In the Specification

In Column 3, Line 24, delete "cylcohexane," and insert -- cyclohexane, --, therefor.

In Column 3, Line 26, delete "imidizoles," and insert -- imidazoles, --, therefor.

In Column 3, Line 49, delete "propyne" and insert -- propyne, --, therefor.

In Column 4, Line 10, delete "arboresent" and insert -- arborescent --, therefor.

In Column 6, Line 45, delete "bonds" and insert -- bonds. --, therefor.

Signed and Sealed this
Ninth Day of July, 2013

Teresa Stanek Rea
*Acting Director of the United States Patent and Trademark Office*

CERTIFICATE OF CORRECTION (continued)
U.S. Pat. No. 8,382,889 B1

In the Specification

In Columns 7 & 8, in Chemical Structure, delete " 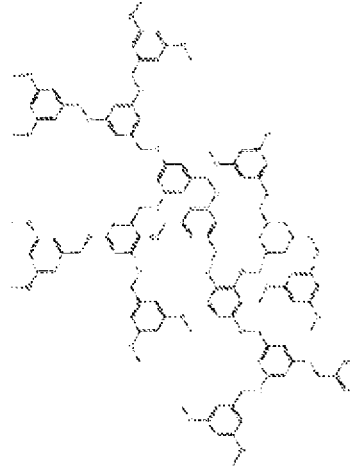 " and insert -- 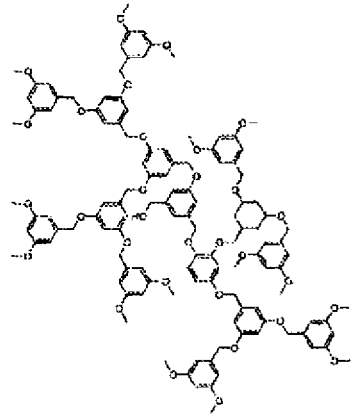 --, therefor.

In Column 11, Line 18, delete "embodiments,a" and insert -- embodiments, a --, therefor.

In Column 11, Line 52, delete "in some" and insert -- In some --, therefor.

In Column 14, Line 17, delete "tertbutanol" and insert -- tert-butanol --, therefor.

In Column 15, Line 58, delete "1,3,5-triodobenzene" and insert -- 1,3,5-triiodobenzene --, therefor.

In Column 21, Line 16, delete "HO–(CH2)x-NR3X" and insert -- HO–$(CH_2)_x$-$NR_3X$ --, therefor.

In Column 22, Line 23, delete "(EtO)2(O)P–(CH2)x-NR3X" and
insert -- (EtO)2(O)P–$(CH_2)_x$-$NR_3X$ --, therefor.

In Column 23, Line 2, delete "tiethylphosphite" and insert -- triethylphosphite --, therefor.

In Column 23, Line 5, delete "Arbusov" and insert -- Arbuzov --, therefor.

In Column 24, in Chemical Structure,

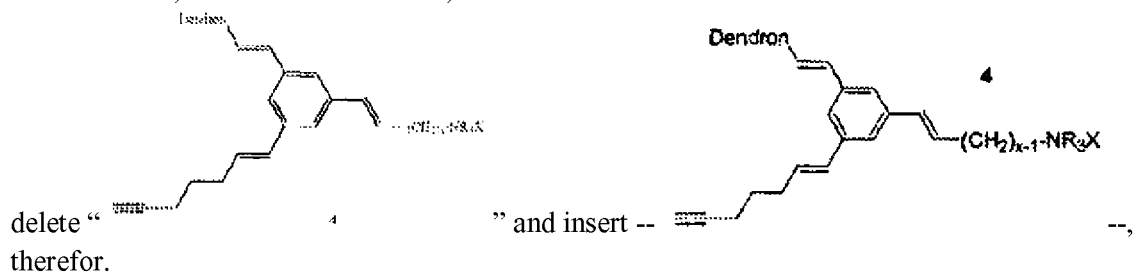

therefor.

In Column 26, Line 33, delete "Stormert" and insert -- Stormer --, therefor.

In the Claims

In Column 29, Line 12, in Claim 3, delete "claim 2," and insert -- claim 2, wherein --, therefor.

In Column 29, Line 16, in Claim 4, delete "claim 2," and insert -- claim 2, wherein --, therefor.

In Column 29, Lines 16-17, in Claim 4, delete "quatrernary" and insert -- quaternary --, therefor.

In Column 29, Line 42, in Claim 9, delete "oligometer" and insert -- oligomer --, therefor.

In Column 29, Line 45, in Claim 10, delete "wherein," and insert -- wherein --, therefor.

In Column 31, Lines 1-16, in Claim 20,

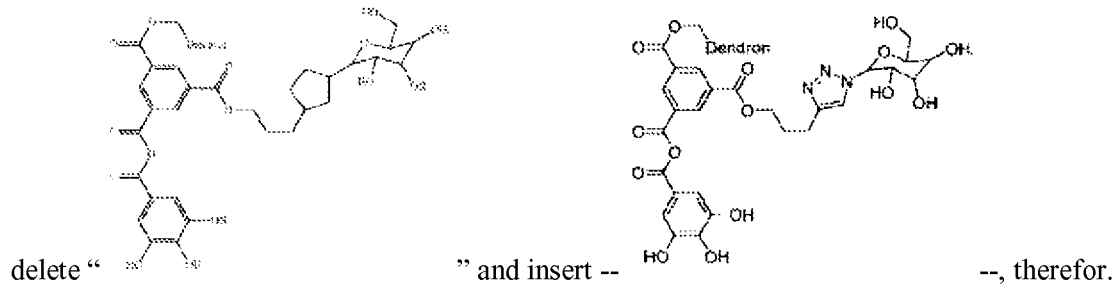

delete " " and insert -- --, therefor.

In Column 31, Line 21, in Claim 21, delete "claim 14," and insert -- claim 1, --, therefor.

In Column 32, Line 30, in Claim 30, delete "mocrobial" and insert -- microbial --, therefor.